United States Patent [19]

Mulder et al.

[11] 4,412,089

[45] Oct. 25, 1983

[54] PROCESS FOR THE PREPARATION OF DIENES AND/OR TRIENES

[75] Inventors: Nicolaas Mulder; Willem Terlouw; Jan H. Wevers, all of Amsterdam, Netherlands

[73] Assignee: Shell Oil Company, Houston, Tex.

[21] Appl. No.: 399,040

[22] Filed: Jul. 16, 1982

[30] Foreign Application Priority Data

Aug. 24, 1981 [GB] United Kingdom ............... 8125781

[51] Int. Cl.³ ............................................... C07C 6/00
[52] U.S. Cl. .................................. 585/645; 585/600; 585/613; 585/646; 585/647
[58] Field of Search ............... 585/600, 613, 645, 646, 585/647

[56] References Cited

U.S. PATENT DOCUMENTS 3,634,539 1/1972 Alkema et al. ..................... 585/353
3,637,891 1/1972 McGrath et al. .................... 585/646
3,855,338 12/1974 Fitton et al. ........................ 585/647

FOREIGN PATENT DOCUMENTS 1532981 11/1978 United Kingdom.
1552368 9/1979 United Kingdom.

*Primary Examiner*—Curtis R. Davis
*Attorney, Agent, or Firm*—Ronald R. Reper

[57] ABSTRACT

Process for the preparation of dienes and/or trienes comprising reacting a polyolefinically unsaturated compound in the presence of a heterogeneous disproportionation catalyst with a compound according to the general formula

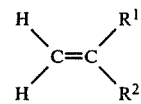

wherein $R^1$ and $R^2$, which may be the same or different, each represents an alkyl, aryl, alkaryl or aralkyl group which may or may not contain one or more inert substituents or $R^1$ and $R^2$ form part of a cyclic structure together with the carbon atom to which they are attached. Isononadiene (2,6-dimethyl-1,5-heptadiene) and/or 2,6,10-trimethyl-1,5,9-undecatriene can be obtained by reacting cis-1,4-polyisoprene with isobutene in the presence of a heterogeneous disproportionation catalyst.

7 Claims, No Drawings

PROCESS FOR THE PREPARATION OF DIENES AND/OR TRIENES

BACKGROUND OF THE INVENTION

The present invention relates to a process for the preparation of dienes and/or trienes by treating polymers with certain olefins in the presence of a disproportionation catalyst. The present invention relates in particular to a process for the preparation of dienes and/or trienes by treating polymers based on conjugated dienes having four or five carbon atoms with certain olefins in the presence of a disproportionation catalyst. Particularly, the present invention relates to a process for the preparation of at least one of isononadiene (2,6-dimethyl-1,5-heptadiene) and 2,6,10-trimethyl-1,5,9-undecatriene by treating polyisoprene with isobutene in the presence of a disproportionation catalyst.

It is known from British Pat. No. 1,264,127 that certain polymers can be broken down into smaller polyolefins by reacting them with a non-conjugated non-alpha olefinically unsaturated non-cyclic hydrocarbon in the presence of a complex homogeneous disproportionation catalyst. Alpha (or terminal) olefins have been suggested as suitable treating agents in, inter alia, U.S. Pat. Nos. 3,912,703 and 3,558,589, the latter disclosing preference for the use of internal olefins over terminal olefins.

A specific class of terminal olefins comprises alpha-olefins having two hydrogen atoms at the terminal carbon atom and no hydrogen atoms attached to the other carbon atom forming the terminal double bond, such as isobutene or derivatives thereof. This class of olefins appears to be rather unsuitable and is explicitly excluded in the definition of the olefinic reactants in both U.S. Pat. No. 3,912,703 (not complying with the definition of "non-tertiary acyclic olefin", column 4, lines 49-54) and British Pat. No. 1,264,127 (not complying with the structure given on page 3, line 57). Moreover, it was found that isobutene did not give a disproportionation reaction in the presence of a homogeneous disproportionation catalyst as disclosed in the aforementioned British Pat. No. 1,264,127; not even in the presence of a suitable olefin like cis-butene-2. The main reaction products observed originated from oligomerization and polymerization reactions.

It has now surprisingly been found that alpha-olefins having two hydrogen atoms at the terminal carbon atom and no hydrogen atoms attached to the other carbon atom forming the terminal double bond can be used to prepare dienes and/or trienes from polymers in the presence of a heterogeneous disproportionation catalyst.

SUMMARY OF THE INVENTION

The present invention therefore relates to a process for the preparation of dienes and/or trienes by reacting a polyolefinically unsaturated compound in the presence of a heterogeneous disproportionation catalyst with a compound according to the general formula

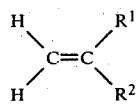

I wherein $R^1$ and $R^2$, which may be the same or different, each represents an alkyl, aryl, alkaryl or aralkyl group and which may or may not contain one or more inert substituents or $R^1$ and $R^2$ form part of a cyclic structure together with the carbon atom to which they are attached.

The present invention relates to particular to a process for the preparation of dienes and/or trienes by reacting a polyolefinically unsaturated compound based on conjugated dienes having four or five carbon atoms with a compound according to formula I wherein $R^1$ and $R^2$, which are the same or different, each represents an alkyl group in the presence of a heterogeneous disproportionation catalyst.

Particularly, the present invention relates to a process for the preparation of 2,6-dimethyl-1,5-heptadiene and/or 2,6,10-trimethyl-1,5,9-undecatriene by reacting polyisoprene with isobutene in the presence of a heterogeneous disproportionation catalyst.

DESCRIPTION OF THE PREFERRED EMBODIMENTS

The use of a heterogeneous catalyst in the process according to the present invention is advantageous not only in that alpha-olefins having two hydrogen atoms at the terminal carbon atom and no hydrogen atoms attached to the other carbon atoms forming the double bond can be used as starting materials, but also in that the product composition of the dienes and trienes can be governed to a high extent by the process conditions. It has been found, for instance, that the ratio of 2,6-dimethyl-1,5-heptadiene (isononadiene) and 2,6,10-trimethyl-1,5,9-undecatriene obtained by reacting polyisoprene, especially cis-1,4-polyisoprene, with isobutene can be varied quite conveniently by slightly changing process conditions such as temperature. It is even possible to prepare almost exclusively 2,6-dimethyl-1,5-heptadiene when carrying out the process according to the present invention in a continuous manner.

The dienes and trienes obtained according to the process according to the present invention are useful intermediates in the production of various chemicals such as aroma chemicals, vitamin E and mercaptans.

Suitable polyolefinically unsaturated compounds, in particular polyolefinically unsaturated hydrocarbons, comprise compounds having a molecular weight of at least 300, which contain one or more recurrent structures in their molecules, while each molecule contains at least five olefinically unsaturated double bonds; if more than one recurrent structure is present, the different recurrent structures may alternate, may be present in a random sequence or in blocks.

Very suitably, a polyolefinically unsaturated hydrocarbon polymer is prepared by polymerization or copolymerization of hydrocarbon monomers, at least part of which monomers contain one or more olefinically unsaturated double bonds after they have been incorporated in the polymer.

Very suitable monomers for the preparation of the polymers or copolymers to be converted are acyclic dienes or polyenes, in particular dienes and preferably conjugated dienes such as butadiene and, in particular, isoprene.

Monomers which can be copolymerized with these dienes and polyenes and which after having been incorporated in the polymer do not contain one or more olefinically unsaturated doulbe bonds are hydrocarbon monomers which contain only one olefinically unsaturated doulbe bond, such as alkenes and aromatic compounds containing one olefinically unsaturated bond. In the class of alkenes, the 1-alkenes are very eligible, in particular the 1-alkenes having up to 12 carbon atoms; propene, 1-butene, isobutene, 1-pentene and 1-hexene are especially suitable. In the class of aromatic compounds containing one olefinically unsaturated bond to be used as co-monomer for the preparation of the polymer, compounds wherein the olefinically unsaturated bond is in conjugation with the aromatic ring are very suitable, and in this class, the compounds having an alpha-olefinically unsaturated bond are in particular suitable. As examples may be mentioned styrene, alpha-methylstyrene, 2-methylstyrene, 3-methylstyrene and 4-methylstyrene; styrene is in particular eligible.

Examples of suitable polymers which can be obtained by homopolymerization of dienes or polyenes are polybutadiene and polyisoprene; examples of suitable polymers which can be obtained by copolymerization of one or more dienes and/or polyenes with one or more hydrocarbon monomers which contain one olefinically unsaturated bond are copolymers of butadiene and styrene and copolymers of isoprene and isobutene.

It is also possible to use naturally occurring polyolefinically unsaturated compounds such as squalene.

The initial molecular weight of the polymer to be used as a starting material in the process according to the present invention may be in the range of from 300 to 5,000,000. Preferably, the molecular weight is in the range of from about 5,000 to about 1,000,000, molecular weight as used herein being defined as weight-average molecular weight. Very good results can be obtained using polymers having an initial molecular weight between 150,000 and 400,000.

The higher the cis-content of the polymer, the better the product selectivity to 2,6-dimethyl-1,5-heptadiene. Cis-1,4-polyisoprene, having a cis-content of at least 95%, preferably at least 98%, appeared to be a very good starting material for the production of 2,6-dimethyl-1,5-heptadiene and 2,6,10-trimethyl-1,5,9-undecatriene.

It is, of course, also possible to subject the high-molecular-weight polymers to a depolymerization treatment prior to the reaction with a compound according to formula I in the presence of a heterogeneous disproportionation catalyst (or to start with lower molecular weight polymers). A convenient technique to obtain lower molecular weight polymers comprises thermal depolymerization, e.g. at temperatures of up to 350° C., preferably under reduced pressure. Depending on the temperature and time, polymers with a molecular weight between 50,000 and 5,000 will be obtained, which are convenient starting materials in the process according to the present invention.

Examples of compounds according to formula I which can be used suitably in the process according to the present invention comprise compounds wherein $R^1$ and $R^2$, which may be the same or different, each represents an alkyl group of up to 6 carbon atoms, an alkaryl, aralkyl or aryl group having up to 12 carbon atoms or $R^1$ and $R^2$, together with the carbon atom to which they are attached, form a cycloalkyl or cycloalkenyl group having at least 5 carbon atoms. Preferred compounds according to formula I are those wherein $R^1$ and $R^2$ are (dis)similar and represent alkyl groups having up to 4 carbon atoms, preferably methyl or ethyl groups or aryl groups, especially phenyl groups, or, together with the carbon atom to which they are attached, form a cyclopentyl, cyclohexyl or cyclohexenyl group. Preferred compounds according to formula I comprise isobutene, 2-methyl-butene-1 and limonene; isobutene is particularly preferred.

The amount of compound according to formula I to be used in the process according to the present invention is, of course, governed by the result desired. When dienes are the preferred product, at least such an amount of a component according to formula I should be used that the total number of double bonds present therein is at least equal to, and preferably exceeds the total number of double bonds present in the polyolefinically unsaturated compound. Normally, good results will be obtained when using a molar excess of compound according to formula I in the range of from 2 to 20, preferably of from 2 to 10, calculated on the molar amount of polyolefinically unsaturated compound applied. When trienes are to be produced predominantly, the total number of double bonds present in the compound according to formula I should be less than the total number of double bonds present in the polyolefinically unsaturated compound; preferably, a ratio of 0.5–0.8 should be applied.

It is also possible to co-produce tetraenes in the process according to the present invention. Use can be made of such compounds, especially of the tetraene containing 19 carbon atoms in the molecule, as intermediates for valuable chemicals such as phytol.

The process according to the present invention will be performed in the presence of a heterogeneous disproportionation catalyst. Examples of suitable catalysts comprise the oxides of molybdenum, cobalt, tungsten and rhenium, especially rhenium. In particular, supported catalysts can be used advantageously in the process according to the present invention. Examples of suitable supports comprise silica, alumina, silica-alumina and aluminum phosphate. Preference is given to the use of rhenium heptoxide on silica or alumina. Any amount of metal oxide (on a carrier) which exhibits disproportionation activity can be used in the process according to the present invention. Amounts of from 0.01%w up to 30%w, or even higher calculated on carrier, can be used. Preference is given to the use of an amount of hetergeneous catalyst in the range of from 1%w to 25%w, calculated on carrier.

If desired, the catalytic system may also contain further catalytically active component(s). This may be one of the metal oxides already mentioned and/or may be another metal compound exerting promoting activity. Examples of combinations of heterogeneous catalyst systems comprise mixtures of tungsten oxide and rhenium heptoxide and molybdenum oxide and rhenium heptoxide, the former mixture being preferred. The weight ratio of the constituting metal oxides may vary widely, e.g. between 1:10 and 10:1. Good results have been obtained using a tungsten/rhenium weight ratio of 3:1. Examples of suitable promoters comprise alkali and alkaline earth metal derivatives such as derivatives of lithium, sodium, potassium, rubidium, cesium, berylium, magnesium, calcium and barium. Preference is given to the use of potassium, cesium and magnesium derivatives, especially the appropriate oxides. The amount of promoter present in the catalytic system is not critical and can vary between wide limits. Good results can be obtained using a promoter in an amount of from 0.05%w–10%w, calculated on carrier, preference being given to amounts in the range of from 0.2%w–5%w, calculated on carrier.

The catalytic system can be suitably subjected to an activating treatment. A suitable treatment comprises heating the catalytic system at elevated temperatures, e.g. at temperatures between 300° C. and 900° C. in an inert atmosphere.

It will be clear that the various catalytic systems exhibit different optimum reaction temperatures, pressures and contact times which can be readily established by those skilled in the art.

If desired, the process according to the present invention can be carried out in the presence of a solvent. Suitable solvents comprise alkanes and isoalkanes such as hexane, heptane, isopentane and isooctane, cycloalkanes such as cyclopentane and cyclohexane and aromatic hydrocarbons such as benzene, toluene, and the xylenes. Also, mixtures of solvents can be readily applied. It is also possible to use one or more of the reaction products such as 2,6-dimethyl-1,5-heptadiene and/or 2,6,10-trimethyl-1,5,9-undecatriene as solvent. An excess of a compound according to formula I can also serve as solvent. For instance, isobutene can be used suitably as a solvent, especially when the reaction is carried out at temperatures below 0° C.

It will be understood that the use of a solvent becomes more advantageous when polyolefinically unsaturated compounds having higher molecular weights are applied as starting materials. It is also possible to partially depolymerize polyolefinically unsaturated compounds in the presence of a solvent for the partially depolymerized starting materials. Depending on the molecular weight obtained, solutions of partially depolymerized polyolefinically unsaturated compounds of more than 25%w, or even higher than 50%w on solvent applied can be obtained.

The process according to the present invention will normally be carried out at moderate temperatures. Temperatures in the range of from −50° C. to +100° C. can be suitably applied. The use of higher temperatures should be avoided because of the increasing possibility of isomerization reactions and other side reactions. Preferred temperatures are in the range of from −25° C. to +35° C.

The process according to the present invention can be carried out at atmospheric and preferably at superatmospheric pressure. Pressures up to 50 bar can be suitably used, but higher pressures are by no means excluded. Good results have been obtained using pressures in the range of from 1 to 30 bar.

The process according to the present invention can be carried out batchwise, semi-continuously and continuously. Depending on the product(s) desired, preference will be given to a batchwise or a continuous process. It has been found that 2,6-dimethyl-1,5-heptadiene can be obtained with a selectivity of almost 100% when the process according to the present invention is carried out continuously allowing a sufficient contact time using poly-cis-isoprene as the polyolefinically unsaturated material. When the process is carried out continuously or batchwise using rather short contact times, a mixture of 2,6-dimethyl-1,5-heptadiene and 2,6,10-trimethyl-1,5,9-undecatriene will be obtained. The composition of the mixture obtained is to some extent dependent on the temperature applied.

The reaction product(s) can be worked up after termination of the reaction by methods known in the art. The product(s) can be obtained suitably by distillation. When the process according to the present invention is carried out continuously part or all of the solvent employed, if any, can be recycled, if desired, together with a substantial amount of trienes and/or tetraenes, depending on the specific reaction conditions applied.

The invention will now be illustrated by means of the following Examples.

CATALYST PREPARATION

The catalysts were prepared by impregnating gamma-alumina with the appropriate amounts of aqueous solutions of potassium carbonate, rhenium heptoxide and ammonium metatungstate. The water was removed by evaporation. The dried composition was calcinated in air at 520° C. for 3 hours.

EXAMPLE 1

2.5 g of a 20%w $Re_2O_7$/2%w $K^+$/$Al_2O_3$ catalyst was activated under nitrogen at 520° C. for 4 hours. 25 ml isooctane was added to the catalyst under nitrogen and the mixture was saturated with isobutene at 20° C. 0.5 g solid polyisoprene (M.W. 250,000) and an internal standard were added to the mixture and stirred for 50 hours under nitrogen (20° C., atmospheric). Analysis of the reaction product by gas-liquid chromatography (GLC) (after excluding isobutene and solvent) showed the presence of 64.4% 2,6-dimethyl-1,5-heptadiene, 2,6,10-trimethyl-1,5,9-undecatriene and 2,6,10,14-tetramethyl-1,5,9,13-pentadecatetraene (product ratio: 48:30:22). The remainder were less degradaded products.

EXAMPLE 2

2.5 g of a 20%w $Re_2O_7$/2%w $K^+$/$Al_2O_3$ catalyst was activated under nitrogen at 520° C. for 4 hours. 25 ml isooctane was added to the catalyst under nitrogen and the mixture was saturated with isobutene at 20° C. To this mixture 5 ml 25% (w/w) polyisoprene solution in isooctane (thermic degradaded polyisoprene, M.W. about 10,000) was added, together with 50 µl n-decane as internal standard. The mol ratio isobutene/isoprene-unit=8. After stirring under nitrogen at 20° C. for 75 hours, GLC analysis showed that 2,6-dimethyl-1,5-heptadiene had been obtained in 91.7% yield.

EXAMPLE 3

2.5 g of a 5%w $Re_2O_7$/15%w $WO_3$/2%w $K^+$/$Al_2O_3$ catalyst was activated under nitrogen at 520° C. for 4 hours. 25 ml isooctane was added to the catalyst under nitrogen and the mixture was saturated with isobutene at 20° C. To this mixture 5 ml 25% (w/w) polyisoprene solution in isooctane (thermic degradaded polyisoprene, M.W. about 7,000) was added, together with 50 µl n-decane as internal standard. The mol ratio isobutene/isoprene unit=7. After stirring for 24 hours at 20° C. the product contained the following compounds (based on % by weight related to the polyisoprene intake):
24.8% 2,6-dimethyl-1,5-heptadiene
10.0% 2,6,10-trimethyl-1,5,9-undecatriene, and
15.1% 2,6,10,14-tetramethyl-1,5,9,13-pentadecatetraene.

EXAMPLE 4

2.5 g of a 20%w $Re_2O_7$/1%w $K^+$/$Al_2O_3$ catalyst was activated under nitrogen at 250° C. for 4 hours. 25 ml isooctane was saturated with isobutene at 20° C. and after cooling to 0° C. added to the activated catalyst under nitrogen. 5 ml 25% (w/w) polyisoprene solution in isooctane (thermic degradaded polyisoprene, M.W.

about 7,000) was added together with 50 μl n-decane as internal standard. The mol ratio isobutene/isoprene unit=8.5. The reaction mixture was stirred under nitrogen at 0° C. for 28 hours followed by GLC analysis. Based on % by weight, related to the polyisoprene-intake, the following products were obtained:
23.5% 2,6-dimethyl-1,5-heptadiene
18.3% 2,6,10-trimethyl-1,5,9-undecatriene
16.9% 2,6,10,14-tetramethyl-1,5,9,13-pentadecatetraene

EXAMPLE 5

30 g of a 20%w $Re_2O_7$/0.5%w $K^+/Al_2O_3$ catalyst was loaded into a stainless steel reactor tube. The catalyst was activated at 530° C. under nitrogen for 5 hours and then cooled to −25° C. At 125 psig and −22° C. a mixture of 35% (w/w) polyisoprene solution in isooctane (thermic degradaded polyisoprene, M.W. about 7,000) and isobutene (volume ratio: 1/5) was passed through the reactor tube (at a liquid hourly space velocity of 2) over a period of 50 hours. The mol ratio isobutene/isoprene unit=10. n-Decane was used as an internal standard for polyisoprene. The collected product was analyzed by GLC and was found to contain, after exclusion of isobutene and isooctane (based on % by weight of the polyisoprene intake):
20.5% 2,6-dimethyl-1,5-heptadiene
11.7% 2,6,10-trimethyl-1,5,9-undecatriene, and
8.8% 2,6,10,14-trimethyl-1,5,9,13-pentadecatetrane.

EXAMPLE 6

2.5 g of a 20%w $Re_2O_7$/2%w $K^+/Al_2O_3$ catalyst was activated under nitrogen at 520° C. for 4 hours. 25 ml n-pentane was added to the catalyst at 20° C. under nitrogen, saturated with isobutene at atmospheric pressure and 0.5 ml of squalene was added. During 25 hours the reaction mixture was stirred at 20° C. and kept saturated with isobutene. Analysis of the reaction products by GLC (% by weight, after excluding isobutene and solvent) showed the presence of:
73.1% 2,6-dimethyl-1,5-heptadiene
21.3% 2,7-dimethyl-2,6-octadiene, and
5.6% higher boiling products.

We claim:

1. Process for the preparation of at least one of 2,6-dimethyl-1,5-heptadiene and 2,6,10-trimethyl-1,5,9-undecatriene by reacting at a temperature in the range from 50° to 100° C. and a pressure up to 50 bar polyisoprene having a molecular weight in the range from about 5,000 to about 1,000,000 with isobutene in the presence of a heterogeneous diaproportionation catalyst.

2. Process according to claim 1 wherein the isobutene is used in a molar excess in the range of from 2 to 20, calculated on the molar amount of polyisoprene.

3. Process according to claim 1 wherein said catalyst comprises an oxide of a metal selected from molybdenum, cobalt, tungsten and rhenium.

4. Process according to claim 1 wherein said catalyst comprises, in addition, at least one compound of a metal selected from alkali and alkaline earth metals.

5. Process according to claim 4, wherein said catalyst is supported on a carrier and at least one compound of an alkali or alkaline earth metal is present in an amount in the range of from 0.05%w to 10%w, calculated on carrier.

6. Process according to claim 1 wherein the process is carried out in the presence of a solvent.

7. Process according to claim 1 wherein said reaction is carried out at a temperature in the range of from −25° C. to +35° C. and a pressure in the range of from 1 to 30 bar.

* * * * *